United States Patent
Powell et al.

(10) Patent No.: US 12,299,635 B2
(45) Date of Patent: *May 13, 2025

(54) MULTI-FACTOR AUTHENTICATION FOR REMOTE ACCESS OF PATIENT DATA

(71) Applicant: AirStrip IP Holdings, LLC, San Antonio, TX (US)

(72) Inventors: William Cameron Powell, San Antonio, TX (US); Stephen Trey Moore, San Antonio, TX (US)

(73) Assignee: AirStrip IP Holdings, LLC, San Antonio, TX (US)

( * ) Notice: Subject to any disclaimer, the term of this patent is extended or adjusted under 35 U.S.C. 154(b) by 923 days.

This patent is subject to a terminal disclaimer.

(21) Appl. No.: 17/201,759

(22) Filed: Mar. 15, 2021

(65) Prior Publication Data
US 2021/0201268 A1  Jul. 1, 2021

Related U.S. Application Data

(63) Continuation of application No. 13/075,903, filed on Mar. 30, 2011, now Pat. No. 10,956,867.
(Continued)

(51) Int. Cl.
*G06F 21/31* (2013.01)
*G06F 21/44* (2013.01)
(Continued)

(52) U.S. Cl.
CPC ............ *G06Q 10/10* (2013.01); *G06F 21/31* (2013.01); *G06F 21/44* (2013.01); *G16H 10/60* (2018.01);
(Continued)

(58) Field of Classification Search
CPC ......... G06F 21/31; G06F 21/44; G16H 10/60; H04L 9/3226; H04L 63/0876;
(Continued)

(56) References Cited

U.S. PATENT DOCUMENTS 5,827,180 A   10/1998  Goodman
5,954,663 A    9/1999  Gat
(Continued)

FOREIGN PATENT DOCUMENTS

CN   1252664 A    5/2000
CN   1270676     10/2000
(Continued)

OTHER PUBLICATIONS

Non-Final Office Action for U.S. Appl. No. 11/301,348 dated Jun. 11, 2009, 26 pages.
(Continued)

*Primary Examiner* — Trong H Nguyen
(74) *Attorney, Agent, or Firm* — Fish & Richardson P.C.

(57) ABSTRACT

The present disclosure is directed to authenticating a mobile device and a user of the mobile device to receive patient data from a clinical information system of a medical facility. In some implementations, methods include receiving a logon request, the logon request comprising credentials and at least one technical factor, accessing a validation database based on the at least one technical factor, determining that the mobile device is an authorized mobile device based on information provided by the validation database and the at least one technical factor, validating the credentials to ensure that the user is authorized to access patient data provided by the clinical information system, and then, upon determining that the user is authorized to access patient data: establishing a session to communicate patient data between the mobile device and the clinical information system, the data managements system processing the patient data communicated during the session.

18 Claims, 6 Drawing Sheets

Related U.S. Application Data

(60) Provisional application No. 61/319,691, filed on Mar. 31, 2010.

(51) Int. Cl.

| | | |
|---|---|---|
| *G06Q 10/10* | (2023.01) | |
| *G16H 10/60* | (2018.01) | |
| *H04L 9/32* | (2006.01) | |
| *H04L 9/40* | (2022.01) | |
| *H04W 12/06* | (2021.01) | |
| *H04W 12/062* | (2021.01) | |
| *H04L 67/12* | (2022.01) | |

(52) U.S. Cl.
CPC ........ *H04L 9/3226* (2013.01); *H04L 63/0876* (2013.01); *H04W 12/062* (2021.01); *H04W 12/068* (2021.01); *H04L 63/083* (2013.01); *H04L 67/12* (2013.01); *H04L 2209/80* (2013.01); *H04L 2209/88* (2013.01)

(58) Field of Classification Search
CPC ... H04L 63/083; H04L 67/12; H04L 2209/80; H04L 2209/88; H04W 12/068
See application file for complete search history.

(56) References Cited

U.S. PATENT DOCUMENTS

| | | | |
|---|---|---|---|
| 5,987,519 | A | 11/1999 | Peifer et al. |
| 6,093,146 | A | 7/2000 | Filangeri |
| 6,168,563 | B1 | 1/2001 | Brown |
| 6,272,469 | B1 | 8/2001 | Koritzinsky et al. |
| 6,302,844 | B1 | 10/2001 | Walker et al. |
| 6,336,900 | B1 | 1/2002 | Alleckson et al. |
| 6,364,834 | B1 | 4/2002 | Reuss et al. |
| 6,383,137 | B1 | 5/2002 | Berry |
| 6,409,659 | B1 | 6/2002 | Warner et al. |
| 6,416,471 | B1 | 7/2002 | Kumar et al. |
| 6,475,146 | B1 | 11/2002 | Frelburger et al. |
| 6,520,910 | B1 | 2/2003 | Kohls |
| 6,523,009 | B1 | 2/2003 | Wilkins |
| 6,587,829 | B1 | 7/2003 | Camarda et al. |
| 6,589,170 | B1 | 7/2003 | Flach et al. |
| 6,616,613 | B1 | 9/2003 | Goodman |
| 6,641,533 | B2 | 11/2003 | Causey, III et al. |
| 6,684,276 | B2 | 1/2004 | Walker et al. |
| 7,038,588 | B2 | 5/2006 | Boone et al. |
| 7,114,174 | B1 | 9/2006 | Brooks |
| 7,242,676 | B2 | 7/2007 | Rao et al. |
| 7,353,179 | B2 | 4/2008 | Ott et al. |
| 7,853,241 | B1* | 12/2010 | Harrison ............ G06Q 10/10 |
| | | | 455/406 |
| 7,974,924 | B2 | 7/2011 | Holla et al. |
| 8,255,238 | B2 | 8/2012 | Powell et al. |
| 9,118,656 | B2 | 8/2015 | Ting et al. |
| 10,078,875 | B2 | 9/2018 | Powell et al. |
| 2001/0044588 | A1 | 11/2001 | Mault |
| 2002/0112155 | A1 | 8/2002 | Martherus et al. |
| 2002/0198473 | A1 | 12/2002 | Kumar et al. |
| 2003/0065626 | A1* | 4/2003 | Allen ............ G06F 21/32 |
| | | | 705/76 |
| 2003/0078806 | A1 | 4/2003 | Kudryk et al. |
| 2003/0085870 | A1 | 5/2003 | Hinckley |
| 2003/0115415 | A1 | 6/2003 | Want et al. |
| 2003/0200226 | A1* | 10/2003 | Wells ............ G06F 16/972 |
| 2003/0236682 | A1 | 12/2003 | Heyer |
| 2004/0034771 | A1* | 2/2004 | Edgett ............ H04L 63/0846 |
| | | | 713/153 |
| 2004/0049476 | A1 | 3/2004 | Sai |
| 2004/0102687 | A1 | 5/2004 | Brashears |
| 2004/0171955 | A1 | 9/2004 | Morganroth |
| 2004/0176983 | A1 | 9/2004 | Birkett |
| 2004/0204635 | A1 | 10/2004 | Scharf et al. |
| 2005/0060198 | A1 | 3/2005 | Bayne |
| 2005/0066061 | A1 | 3/2005 | Graves et al. |
| 2005/0206518 | A1 | 9/2005 | Welch et al. |
| 2006/0149597 | A1 | 7/2006 | Powell et al. |
| 2006/0287890 | A1 | 12/2006 | Stead |
| 2007/0204044 | A1* | 8/2007 | Rice ............ H04L 63/08 |
| | | | 709/225 |
| 2008/0004904 | A1 | 1/2008 | Tran |
| 2008/0021730 | A1 | 1/2008 | Holla et al. |
| 2008/0021834 | A1* | 1/2008 | Holla ............ G16H 80/00 |
| | | | 705/51 |
| 2008/0109447 | A1 | 5/2008 | Mathur |
| 2008/0120707 | A1 | 5/2008 | Ramia |
| 2008/0250340 | A1 | 10/2008 | Dlugos et al. |
| 2009/0062887 | A1 | 3/2009 | Mass et al. |
| 2009/0063701 | A1 | 3/2009 | Bagepalli et al. |
| 2009/0076912 | A1* | 3/2009 | Rajan ............ G06Q 30/0267 |
| | | | 705/14.64 |
| 2010/0050110 | A1 | 2/2010 | Hughes |
| 2010/0056877 | A1* | 3/2010 | Fein ............ G16H 70/60 |
| | | | 705/2 |
| 2010/0235782 | A1 | 9/2010 | Powell et al. |
| 2010/0306858 | A1 | 12/2010 | McLaren et al. |
| 2011/0138175 | A1 | 6/2011 | Clark et al. |
| 2011/0246235 | A1 | 10/2011 | Powell et al. |
| 2013/0030831 | A1 | 1/2013 | Powell et al. |
| 2015/0142737 | A1 | 5/2015 | Behuria |

FOREIGN PATENT DOCUMENTS

| | | | |
|---|---|---|---|
| JP | A 2000-97728 | 4/2000 | |
| JP | 2000316820 | 11/2000 | |
| JP | A 2001-101309 | 4/2001 | |
| JP | A 2004-102756 | 4/2004 | |
| JP | A 2004-230099 | 8/2004 | |
| KR | 20060026623 A * | 3/2006 | ............ G06Q 50/22 |
| WO | WO1999014882 | 11/2000 | |
| WO | WO2002043590 | 6/2002 | |
| WO | WO2004084720 | 10/2004 | |
| WO | WO2005048833 | 6/2005 | |
| WO | WO2006086089 | 8/2006 | |

OTHER PUBLICATIONS

Final Office Action for U.S. Appl. No. 11/301,348 dated Dec. 10, 2009, 22 pages.

International Preliminary Report on Patentability (1 page) dated Jul. 3, 2007 and Written Opinion of the International Searching Authority (3 pages) dated Jun. 5, 2006 for International Application No. PCT/US2006/000035.

International Search Report for International Application No. PCT/US2006/000035, dated Jun. 5, 2006, 2 pages.

Authorized officer Blaine R. Copenheaver, International Search Report and Written Opinion of the International Searching Authority for International Application No. PCT/US2010/026993, mailed May 11, 2010, 8 pages.

Supplementary European Search Report for Application No. 06717260.1, mailed Aug. 2, 2010, 7 pages.

First Office Action for Application No. 200680006961.7, mailed Nov. 2, 2010, 11 pages.

Second Office Action for Application No. 200680006961.7, mailed Apr. 8, 2011, 5 pages.

Second Examination Report for Application No. 2006213066, mailed Feb. 24, 2011, 2 pages.

First Examination Report for Application No. 2006213066, mailed Apr. 23, 2010, 2 pages.

Authorized Officer Philippe Bécamel, International Preliminary Report on Patentability for Application No. PCT/US2010/026993, dated Sep. 22, 2011, 6 pages.

Plaintiffs' Complaint for Patent Infringement, *Airstrip Technologies, Inc. et al.* v. *mVISUM, Inc.*, Civil Action No. 1:12-cv-07776-JFK, United States District Court for the Southern District of New York, Document 1, filed Oct. 18, 2012, 30 pages.

Defendant's Answer and Counterclaim, *Airstrip Technologies, Inc. et al.* v. *mVISUM, Inc.*, Civil Action No. 1:12-cv-07776-JFK, United

(56) References Cited

OTHER PUBLICATIONS

States District Court for the Southern District of New York, Document 29, filed Apr. 5, 2013, 13 pages.
GE Healthcare, "Web Viewer and Pocket Viewer," 2007, retrieved from http://www3.gehealthcare.com/~/media/Downloads/US/Product/Product-Categories/Patient-Monitoring/Careports/Mobile-Viewers/GEHealthcare-Web-Viewer-Pocket-Viewer-ProductSpec.pdf?Parent=%7B1ED25767-3F69-413B-8C56-3DDEA5CEF31F%7D, 4 pages.
Edward H. Schmuhl et al., "HP Palm Vue: A New Healthcare Information Product," Hewlett-Parkard Journal, Article 8, Jun. 1996, retrieved from http://www.hpl.hp.com/hpjournal/96jun/jun96a8.pdf, pp. 12-17.
MobileInfo, "Data Critical's Stat View™ Alarm Notification System," Jun. 2000, retrieved from http://www.mobileinfo.com/Applications_Vertical/Healthcare_Applications/StatView.htm, 2 pages.
Telecompaper, "Data Critical Launches Rhythmstat XL Medical System," Jan. 8, 1998, retrieved from http://www.telecompaper.com/news/data-critical-launches-rhythmstat-xl-medical-system--26725, 2 pages.
U.S. Food and Drug Administration, Protecting and Promoting Your Health, "MAUDE Adverse Event Report: Data Critical Corp. Impactpaging System," Nov. 19, 2000, retrieved on Apr. 8, 2013 from <www.accessdata.fda.gov/scripts/cdrh/cfdocs/cfmaude/detail.cfm?mdrfoi_id=312735>, 2 pages.
Department of Health & Human Services, Food and Drug Administration, Center for Devices and Radiological Health, 510(k) Summary and approval letter for FlexView™ Clinical Monitoring System (K003998), Mar. 7, 2001, 4 pages.
Department of Health & Human Services, Food and Drug Administration, Center for Devices and Radiological Health, 510(k) Summary and approval letter for AlarmView™ Wireless Data Network System (K010912), Apr. 5, 2001, 4 pages.
Department of Health & Human Services, Food and Drug Administration, Center for Devices and Radiological Health, 510(k) Summary and approval letter for Agilent Information Center (AIC) Software Release D.0 (K011093), May 1, 2001, 5 pages.
Department of Health & Human Services, Food and Drug Administration, Center for Devices and Radiological Health, 510(k) Summary and approval letter for Mobile-PatientViewer™ (K011436), Jul. 5, 2001, 5 pages.
Department of Health & Human Services, Food and Drug Administration, Center for Devices and Radiological Health, 510(k) Summary and approval letter for FlexView™ Clinical Monitoring System (K011999), Jul. 24, 2001, 4 pages.
Department of Health & Human Services, Food and Drug Administration, Center for Devices and Radiological Health, 510(k) Summary and approval letter for AlarmView™ Wireless Data Network System (K012005), Jul. 24, 2001, 4 pages.
Department of Health & Human Services, Food and Drug Administration, Center for Devices and Radiological Health, 510(k) Summary and approval letter for AlarmView™ Wireless Data Network System (K013156), Oct. 19, 2001, 4 pages.
Department of Health & Human Services, Food and Drug Administration, Center for Devices and Radiological Health, 510(k) Summary and approval letter for Datex-Ohmeda S/5 Web Viewer, Datex-Ohmeda S/5 Pocket Viewer and Datex-Ohmeda S/5 Cellular Viewer with L-WEB04 software (K052975), Jan. 20, 2006, 7 pages.
Department of Health & Human Services, Food and Drug Administration, Center for Devices and Radiological Health, 510(k) Summary and approval letter for Web Viewer, Pocket Viewer and Cellular Viewer with L-WEB05 software (K061994), Aug. 11, 2006, 4 pages.
Department of Health & Human Services, Food and Drug Administration, Center for Devices and Radiological Health, 510(k) Summary and approval letter for RhythmStat XL System (K971650), Dec. 4, 1997, 9 pages.
Department of Health & Human Services, Food and Drug Administration, Center for Devices and Radiological Health, 510(k) Summary and approval letter for Cardio-Pager™ System (K973527), Mar. 31, 1998, 6 pages.
Department of Health & Human Services, Food and Drug Administration, Center for Devices and Radiological Health, 510(k) Summary and approval letter for Hewlett-Packard M2605A Viridia Wave Viewer (K974567), Jan. 20, 1998, 5 pages.
Department of Health & Human Services, Food and Drug Administration, Center for Devices and Radiological Health, 510(k) Summary and approval letter for StatView™ System (K990378), Sep. 20, 1999, 6 pages.
Department of Health & Human Services, Food and Drug Administration, Center for Devices and Radiological Health, 510(k) Summary and approval letter for AlarmView™ System (K992848), Nov. 19, 1999, 6 pages.
First Examination Report for Application No. 2010224089, mailed Jul. 9, 2013, 3 pages.
First Office Action For Application No. 201080020788.2, mailed Jun. 24, 2013, 13 pages.
Examination Report for Application No. 2,608,497, mailed Jun. 6, 2013, 5 pages.
Second Office Action For Application No. 201080020788.2, mailed Feb. 7, 2014, 11 pages.
Japan Patent Office, Notice of Reasons for Rejection For Application No. 2011-554201, mailed Feb. 12, 2014, 8 pages.
Examination Report for Application No. 06717260.1, mailed Jan. 20, 2014, 4 pages.
European Search Report for Application No. 10751422.6, mailed Jul. 7, 2014, 3 pages.
Examination Report for Application No. 2,608,497, mailed Jul. 30, 2014, 4 pages.
Third Office Action For Application No. 201080020788.2, mailed Sep. 2, 2014, 9 pages.
European Examination Report for Application No. 10751422.6, mailed Aug. 1, 2014, 6 pages.
Nelwan et al. "Ubiquitous mobile access to real-time patient monitoring data." In Computers in Cardiology, 2002 (pp. 557-560). IEEE.
First Examination Report for Indian Application No. 6042/DELNP/2007, mailed Mar. 2, 2015, 2 pages.
Non-final Office Action for U.S. Appl. No. 13/588,539, mailed Apr. 7, 2015, 34 pages.
Examination Report for Application No. 2,608,497, mailed Aug. 11, 2015, 5 pages.
Examination Report for Application No. 2,608,497, mailed Aug. 25, 2016, 4 pages.
Examination Report for Application No. 2,608,497, mailed Jul. 20, 2017, 5 pages.
Examination Report for Application No. 2,608,497, mailed May 16, 2018, 6 pages.

* cited by examiner

MULTI-FACTOR AUTHENTICATION FOR REMOTE ACCESS OF PATIENT DATA

CROSS-REFERENCE TO RELATED APPLICATIONS

This application is a continuation of U.S. application Ser. No. 13/075,903, filed on Mar. 30, 2011, which claims the benefit of U.S. App. No. 61/319,691, filed on Mar. 31, 2010, the disclosure of which are expressly incorporated herein by reference in their entirety.

FIELD

This invention generally relates to systems and methods for transmitting, receiving and displaying data and/or information over wireless communication and data processing devices, and more specifically to systems and methods for multi-factor authentication for accessing medical patient data and/or information from a mobile device.

BACKGROUND

While physicians and other health care providers currently utilize a large number of products and systems that benefit from advances in wireless communication technology, there are still significant limitations to the information that can be transmitted, received, and displayed over these devices in a practical and efficient manner. There are many limitations that are intrinsic to mobile devices, especially those constraints related to speed, performance, memory, and display size. In addition, because of the critical nature of medical data, it is important that the technology work reliably and efficiently over potentially low speed, low bandwidth, and sometimes intermittent wireless connections.

Efforts have been made in the past to transmit medical information through various telecommunication means to health care professionals for review and analysis. Some such efforts are outlined in commonly assigned U.S. patent application Ser. No. 11/301,348, filed on Dec. 12, 2005, the disclosure of which is expressly incorporated herein by reference in its entirety for all purposes. Such examples utilize wireless data communication technologies to transmit medical information to health care providers, or to condition data such that it may be useful for remote monitoring purposes.

SUMMARY

In one aspect, the present invention provides a computer-implemented method for authenticating a mobile device and a user of the mobile device to receive patient data from a clinical information system of a medical facility. In some aspects, the method includes receiving a logon request at a data management system, the logon request comprising credentials and at least one technical factor, accessing, at the data management system, a validation database based on the at least one technical factor, determining, at the data management system, that the mobile device is an authorized mobile device based on information provided by the validation database and the at least one technical factor, validating the credentials to ensure that the user is authorized to access patient data provided by the clinical information system, and then, upon determining that the user is authorized to access patient data, establishing a session to communicate patient data between the mobile device and the clinical information system, the data managements system processing the patient data communicated during the session.

In some aspects, the credentials include a username and a password.

In some aspects, the at least one technical factor includes a device identification associated with the mobile device.

In some aspects, the mobile device comprises a mobile phone, and the at least one technical factor further includes a telephone number associated with the mobile device.

In some aspects, the data management system includes a web server and an application server. The web server operates in a perimeter network and provides services to the application server and an external network, the perimeter network limiting access from the external network to the application server. The web server and the application server can be provided on a common physical device and are logically separated from one another. The web server and the application server can be provided on respective physical devices to be physically separate from one another.

In some aspects, the method further includes transmitting the credentials from the data management system to the clinical information system when it is determined that the mobile device is an authorized mobile device, the clinical information system performing the validating.

In some aspects, the method further includes retrieving authentication information from the information system, the data management system performing the validating based on the authentication information.

In some aspects, the method further includes generating digital patient data and/or patient information at a facility, storing the patient data and/or the patient information in memory of an information system associated with the facility, and copying the patient data and/or the patient information to the data management system, the data management system being remotely located from the facility.

In some aspects, the facility includes a first facility of a facility system, and the data management system is located at a second facility of the facility system.

In some aspects, the facility is a member of a facility system, and the data management system is resident at a third party location, which is outside of the facility system.

In some aspects, the facility is a member of a first facility system, and the data management system communicates with the first facility system and a second facility system.

In some aspects, the method further includes generating the digital patient data using a patient monitoring device that is in communication with the information system.

In some aspects, the method further includes generating the patient information based on user input into the information system.

In other aspects, the invention also provides computer-readable storage device encoded with a computer program comprising instructions that, when executed, operate to cause one or more processors to perform one or more actions in accordance with methods provided herein.

Other aspects of the invention provide system including one or more processors, and a computer-readable storage device coupled to the one or more processors and having instructions stored thereon which, when executed by the one or more processors, cause the one or more processors to perform one or more actions in accordance with methods provided herein.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

The present disclosure provides a healthcare provider with secure, remote access to patient data. The present disclosure builds on that of commonly assigned U.S. patent application Ser. No. 11/301,348, filed on Dec. 12, 2005, the disclosure of which is expressly incorporated herein by reference in its entirety for all purposes. U.S. patent application Ser. No. 11/301,348 claims the benefit of U.S. Prov. App. No. 60/641,057, filed on Jan. 3, 2005, the disclosure of which is also expressly incorporated herein by reference in its entirety for all purposes. For purposes of the instant description, and by way of non-limiting example, implementations of the present disclosure will be described in the context of patient data corresponding to maternity patients (e.g., obstetric (OB) patient). Implementations of the present disclosure are applicable to any variety of patients and corresponding patient data.

Figure 1:
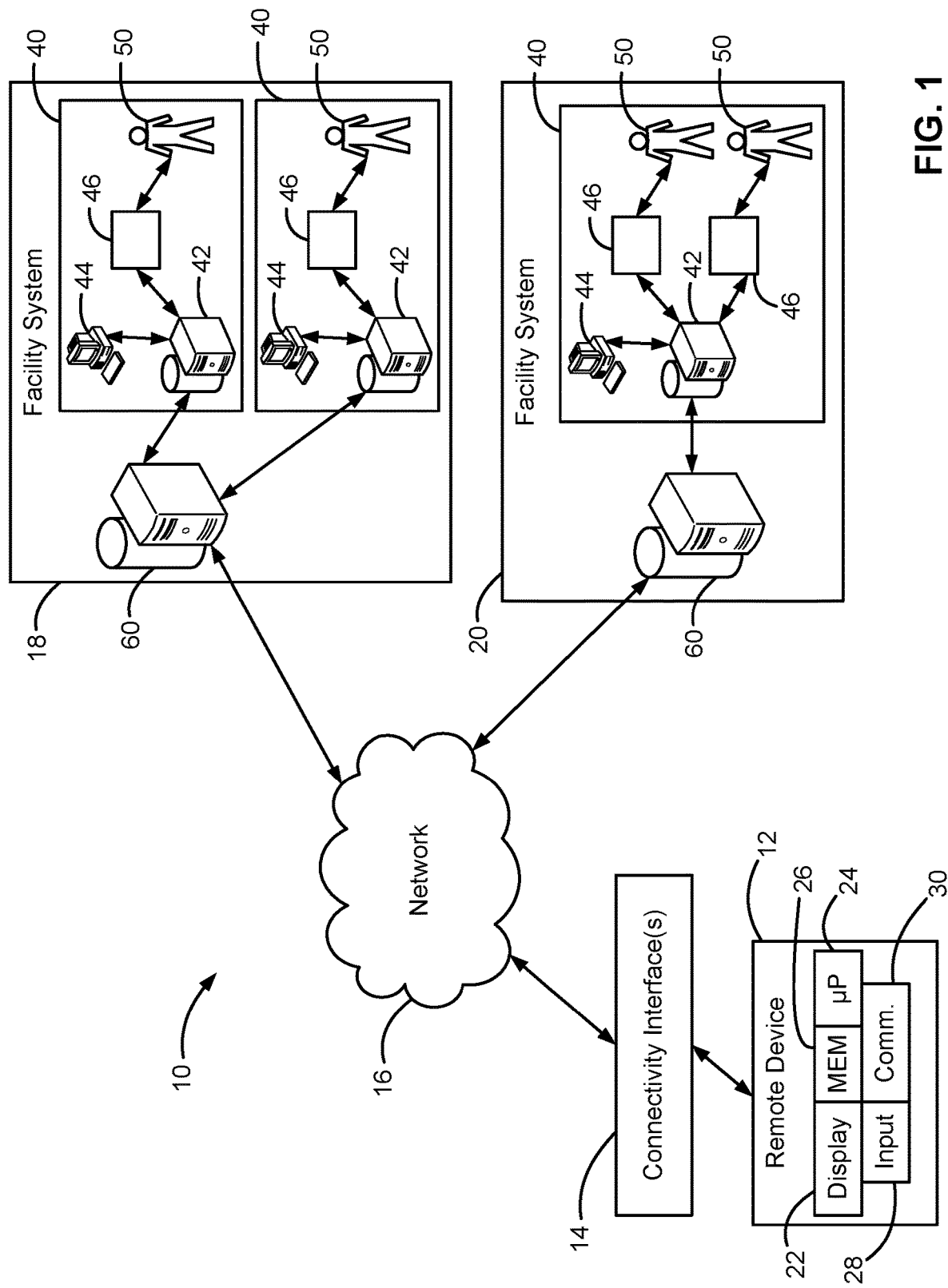
FIG. 1 is a schematic illustration of an exemplar system architecture in accordance with the present disclosure.

Referring now to FIG. 1, an exemplar system architecture 10 is illustrated, and includes a mobile device 12, connectivity interface(s) 14, a network 16, a first facility system 18, and a second facility system 20. As discussed in further detail herein, data is transferred from each of the first and second facility systems 18, 20 through the network 16 and connectivity interface(s) 14 for presentation, or display on the mobile device 12. Further, data can be transferred from the mobile device 12 through the connectivity interface(s) 14 and network 16 to each of the first and second facility systems 18, 20. Although a single mobile device 12 is illustrated, it is contemplated that one or more mobile devices 12 can communicate with each of the first and second facility systems 18, 20 through the network 16 and connectivity interface(s) 14. Similarly, although two facility systems are illustrated, the present disclosure can be implemented with one or more facility systems.

The mobile device 12 can include any number of exemplar devices. Such exemplar devices include, but are not limited to, a mobile phone, a smartphone, a personal digital assistant (PDA), a laptop, a tablet personal computer (PC), a desktop PC, and/or combinations thereof. The mobile device 12 includes a display 22, a processor 24, memory 26, an input interface 28, and a communication interface 30. The processor 24 can process instructions for execution of implementations of the present disclosure. The instructions can include, but are not limited to, instructions stored in the memory 26 to display graphical information on the display 22. Exemplar displays include, but are not limited to, a thin-film-transistor (TFT) liquid crystal display (LCD), or an organic light emitting diode (OLED) display.

The memory 26 stores information within the mobile device 12. In some implementations, the memory 26 can include a volatile memory unit or units, and/or a non-volatile memory unit or units. In other implementations, removable memory can be provided, and can include, but is not limited to, a memory card. Exemplar memory cards can include, but are not limited to, a secure digital (SD) memory card, a mini-SD memory card, a USB stick, and the like.

The input interface 28 can include, but is not limited to, a keyboard, a touchscreen, a mouse, a trackball, a microphone, a touchpad, and/or combinations thereof. In some implementations, an audio codec (not shown) can be provided, which receives audible input from a user or other source through a microphone, and converts the audible input to usable digital information. The audio codec can generate audible sound, such as through a speaker that is provided with the mobile device 12. Such sound may include, but is not limited to, sound from voice telephone calls, recorded sound (e.g., voice messages, music files, etc.), and sound generated by applications operating on the mobile device 12.

The mobile device 12 may communicate wirelessly through the communication interface(s) 14, which can include digital signal processing circuitry. The communication interface(s) 14 may provide communications under various modes or protocols including, but not limited to, GSM voice calls, SMS, EMS or MMS messaging, CDMA, TDMA, PDC, WCDMA, CDMA2000, and/or GPRS. Such communication may occur, for example, through a radio-frequency transceiver (not shown). Further, the mobile device can be capable of short-range communication using features including, but not limited to, Bluetooth and/or WiFi transceivers (not shown).

The mobile device 12 communicates with the network 16 through the connectivity interface(s) 14. The connectivity interface(s) 14 can include, but is not limited to, a satellite receiver, cellular network, a Bluetooth system, a Wi-Fi system (e.g., 802.x), a cable modem, a DSL/dial-up interface, and/or a private branch exchange (PBX) system. Each of these connectivity interfaces 14 enables data to be transmitted to/from the network 16. The network 16 can be provided as a local area network (LAN), a wide area network (WAN), a wireless LAN (WLAN), a metropolitan area network (MAN), a personal area network (PAN), the Internet, and/or combinations thereof.

Figure 2:
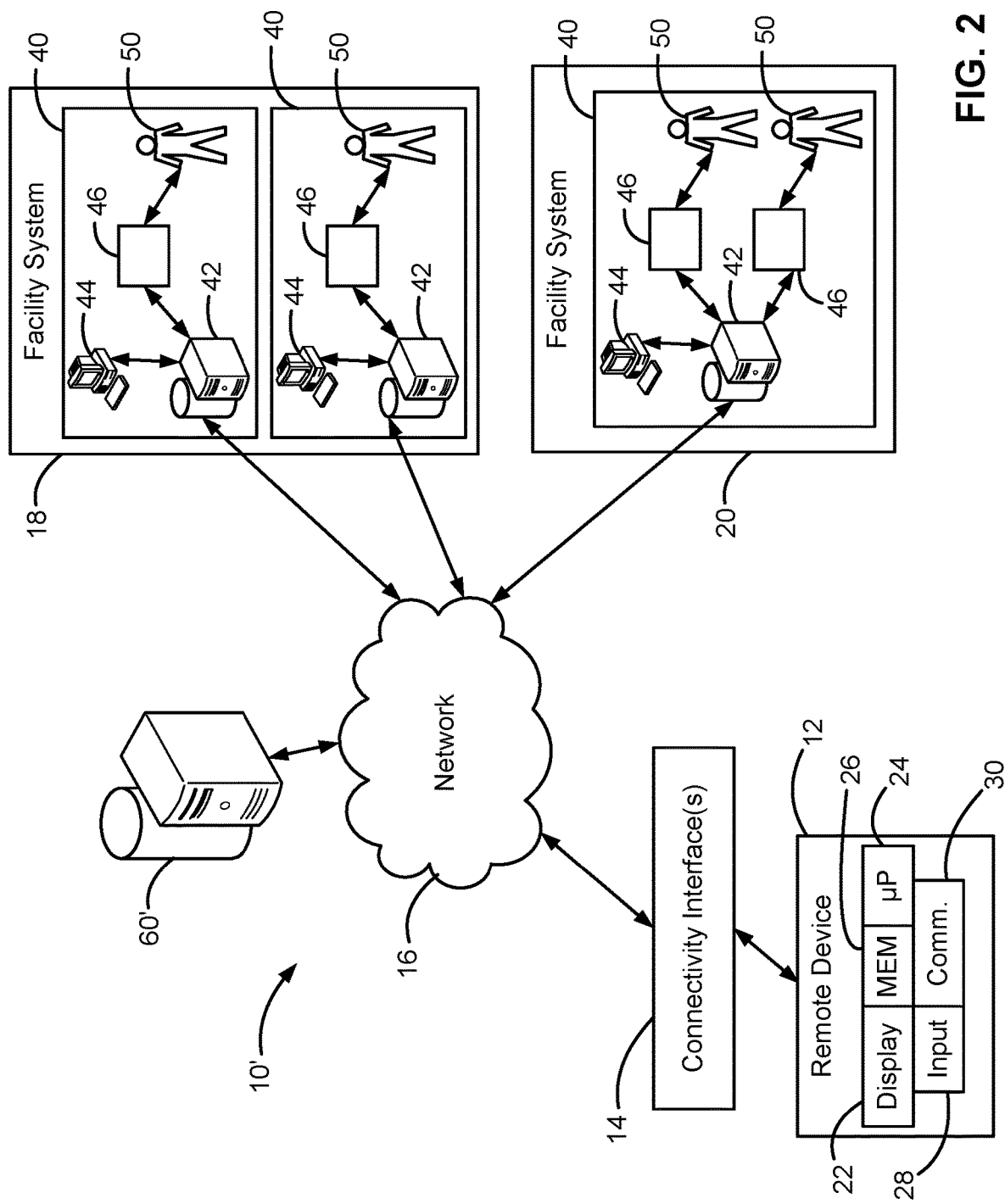
FIG. 2 is a schematic illustration of another exemplar system architecture in accordance with the present disclosure.

In the exemplar systems of FIGS. 1 and 2, the first facility system 18 includes a plurality of facilities 40, and the second facility system 20 includes a facility 40. It is contemplated that each facility system 18, 20 can include one or more facilities, and is not limited to the exemplar arrangement described herein. In the case of multiple facilities, the facilities can be remotely located from one another, and/or can be located at a common location, or site (e.g., separate departments in a common building). Each facility system 18, 20 can be provided as a medical care system, for example, which medical care system can include one or more hospitals, hospital systems, clinics, physician offices, and the like.

Each facility 40 includes an associated information system 42, computer interface(s) 44, and patient monitoring device(s) 46. Exemplar information systems can include, but are not limited to, a clinical information system (CIS), and/or a hospital information system (HIS). Each information system 42 can be provided as a server, and supports the acquisition, storage, modification, and distribution of clinical information, such as patient data, throughout the facility 40 and/or facility system 18, 20. Exemplar information systems include, but are not limited to, the Integriti Enterprise Wide CIS, the QS Perinatal CIS, and/or the QS Critical Care CIS, each provided by General Electric (GE), the OBiX Perinatal Data System provided by Clinical Computer Systems, Inc., the IntelliVue Clinical Information Portfolio (ICIP), Critical Care and/or OB TraceVue Perinatal Data System provided by Royal Philips Electronics, the Essentris Perinatal, Acute Care and/or Critical Care systems provided by CliniComp International, Inc., the CALM Perinatal Data System provided by LMS Medical Systems, the Horizon Lab, Medical Imaging, Cardiology, Emergency Care and/or Perinatal Care provided by McKesson Corporation, and/or the NaviCare WatchChild System provided by Hill-Rom. Each information system 42 can communicate with one or more ancillary information systems (not shown) that can include, but are not limited to, a pharmacy management system, a laboratory management system, and/or a radiology management system. Although the exemplar system architecture 10 includes an information system 42 located at each facility 40, it is contemplated that the facilities 40 can communicate with a common information system 42 that is remotely located from either facility 40, or that is located at one of the facilities 40 within the facility system 18, 20.

The computer interface 44 can communicate with the information system 42 to enable access to information that is stored within, and managed by the information system 42. The computer interface 44 can include, but is not limited to, a personal computer (PC) (e.g., desktop, laptop, or tablet). Although a single computer interface 44 is illustrated in the exemplar architectures described herein, it is contemplated that one or more computer interfaces 44 can communicate with the information system 42. Communication between each computer interface 44 and the information system 42 can be achieved via a direct connection, or remotely through a network (not shown) that can include, but is not limited to, a LAN, a WAN, a WLAN, and/or the Internet.

Each patient monitoring device 46 monitors physiological characteristics of a particular patient 50, and generates data signals based thereon. Exemplar patient monitoring devices include, but are not limited to, maternal/fetal heart rate monitors, blood pressure monitors, respiratory monitors, vital signs monitors, electrocardiogram monitors, oximetry and/or anesthesia monitors. Exemplar patient monitoring devices can include, but are not limited to the Corometric Series Monitors, DINAMAP Series Monitors, DASH Series Monitors, and/or Solar Series monitors provided by GE Healthcare, IntelliVue and/or SureSigns Series patient monitors, and/or Avalon Series Fetal Monitors provided by Royal Philips Electronics, and/or Infinity Series patient monitors provided by Draeger Medical. The data signals are communicated to the information system 42, which collects patient data based thereon, and stores the data to a patient profile that is associated with the particular patient. Although a single patient monitoring device 46 is illustrated per each patient 50, it is contemplated that multiple patient monitoring devices 46 can monitor a particular patient 50. The patient monitoring device(s) 46 can communicate with the information system 42 via a direct connection, or remotely through a network (not shown) that can include, but is not limited to, a LAN, a WAN, a WLAN, and/or the Internet.

The patient data is made available for display on the computer device 44. A healthcare provider (e.g., a nurse and/or physician) can augment the patient data by inputting patient information that is also stored to the information system 44. More specifically, the healthcare provider can input patient information corresponding to a particular patient 50, which patient information can be stored to the patient profile. By way of one non-limiting example, a nurse can input nursing notes, which nursing notes can be stored to the patient profile in the information system. As used herein, the term patient information includes any information corresponding to a patient that is input and stored to the information system 42 through the computer interface 44. Patient information is discussed in further detail below.

As discussed above, each information system 42 stores patient data that can be collected from the patient monitoring devices 46, as well as additional patient information, that can include information that is input by a healthcare provider. The information system 46 communicates the patient data and/or the additional patient data to a data management system (DMS) 60. The DMS 60 can be provided as a server, or a virtual server, that runs server software components, and can include data storage including, but not limited to, a database and/or flat files. In the exemplar system architecture of FIG. 1, each facility system 18, 20 includes a corresponding DMS 60. In such an arrangement, each information system 42 communicates patient data, and/or additional patient data to the DMS 60. Furthermore, and as discussed in further detail below, the DMS 60 can communicate ancillary information to the information system 42. Communication between the DMS 60 and the information system(s) 42 can be achieved via a direct connection, or remotely through a network (not shown) that can include, but is not limited to, a LAN, a WAN, a WLAN, and/or the Internet.

A DMS 60 corresponding to a particular facility system can be remotely located from any of the facilities 40 of the facility system 18, 20, or can be located at a particular facility 40 of the facility system 18, 20. In the exemplar system architecture of FIG. 1, the DMS 60 is remotely located from either facility 40 within each of the facility systems 18, 20. It is contemplated, however, that the DMS 60 can be located at one of the facilities 40, and remote from the other facility 40.

In the exemplar system architecture of FIG. 2, a common DMS 60' is provided. The common DMS 60' is common to various facility systems 18, 20, and is not associated with a particular facility system 18, 20. Each information system 42 communicates with the DMS 60' via a direct connection, or remotely through a network (not shown) that can include, but is not limited to, a LAN, a WAN, a WLAN, and/or the Internet. In the exemplar arrangement of FIG. 2, the DMS 60' communicates with each of the information systems 42 through the network 16. The information systems 42 communicate patient data and/or patient information to the DMS 60', and the DMS 60' can communicate ancillary information to the information system 42, as discussed in further detail below.

In the exemplar system architecture of FIG. 1, the facility 40, or facility system 18, 20 installs the DMS 60 as a local DMS, and the DMS 60 sits at the local site with other servers that can include, but are not limited to, the information system 42. In some implementations, the DMS 60 can be sectioned off, or separated from a logical network perspective, but still physically exists with the other servers that belong to the respective facility 40. Server components are installed on the DMS 60, which components can include, but are not limited to, a database component, a database synchronization component, a web services component, and/or a structured query language (SQL) component. An information system interface can also be installed on the DMS 60, and functions as the interface to the information system 42. By way of non-limiting example, the information system interface can include OBLink, provided by GE Healthcare. In some implementations, the DMS 60 can be arranged in a multiple server configuration, in which one server only hosts web service related components and is logically segregated, and another server has the remaining necessary server components installed.

The exemplar system architecture of FIG. 2, provides for the remote location of data collection at the DMS 60'. In such implementations, the DMS 60' can be provided at a third-party site, remote from any of the facilities 40, or facility systems 18, 20. The third-party functions as a DMS host, and the necessary server components are installed on the remotely hosted DMS 60'. In some implementations, a business-to-business (B2B) virtual private network (VPN) can be created between the remotely hosted DMS 60' and the network of the facility 40 or facility system 18, 20. In this manner, the facility 40 and/or facility system 18, 20 forgoes the purchase and/or maintenance of another physical server, or DMS 60. Further, the up-time and the status of availability of the DMS 60' are easier to manage on the part of a dedicated third-party. The DMS' access to the network can be attended to by the third-party, as opposed to burdening the facility 40, or the facility systems 18, 20. Further, the third-party can implement virtual server technologies to leverage multiple DMS installations on a single physical server. In such implementations, a plurality of virtual servers are logically partitioned in a single physical server, and each virtual server has the capability of running its own operating system and server components, and can be independently booted.

The DMS 60, 60' synchronizes and transfers data between the mobile device 12, or multiple mobile devices 12, and the information system 42, or multiple information systems 42. More specifically, the DMS 60, 60' processes and prepares the patient data and/or patient information for transfer to and presentation on the mobile device 12, or multiple mobile devices 12, from the information system 42. The DMS 60, 60' also processes and prepares ancillary information for transfer to and storage in the information system 42 from the mobile device 12, or multiple mobile devices 12 for potential presentation at a corresponding computer device 44. Exemplar DMSs can include, but are not limited to, the AirStrip Server provided by AirStrip Technologies, LLC, which AirStrip Server includes AirStrip Server Components installed therein.

Figure 3:
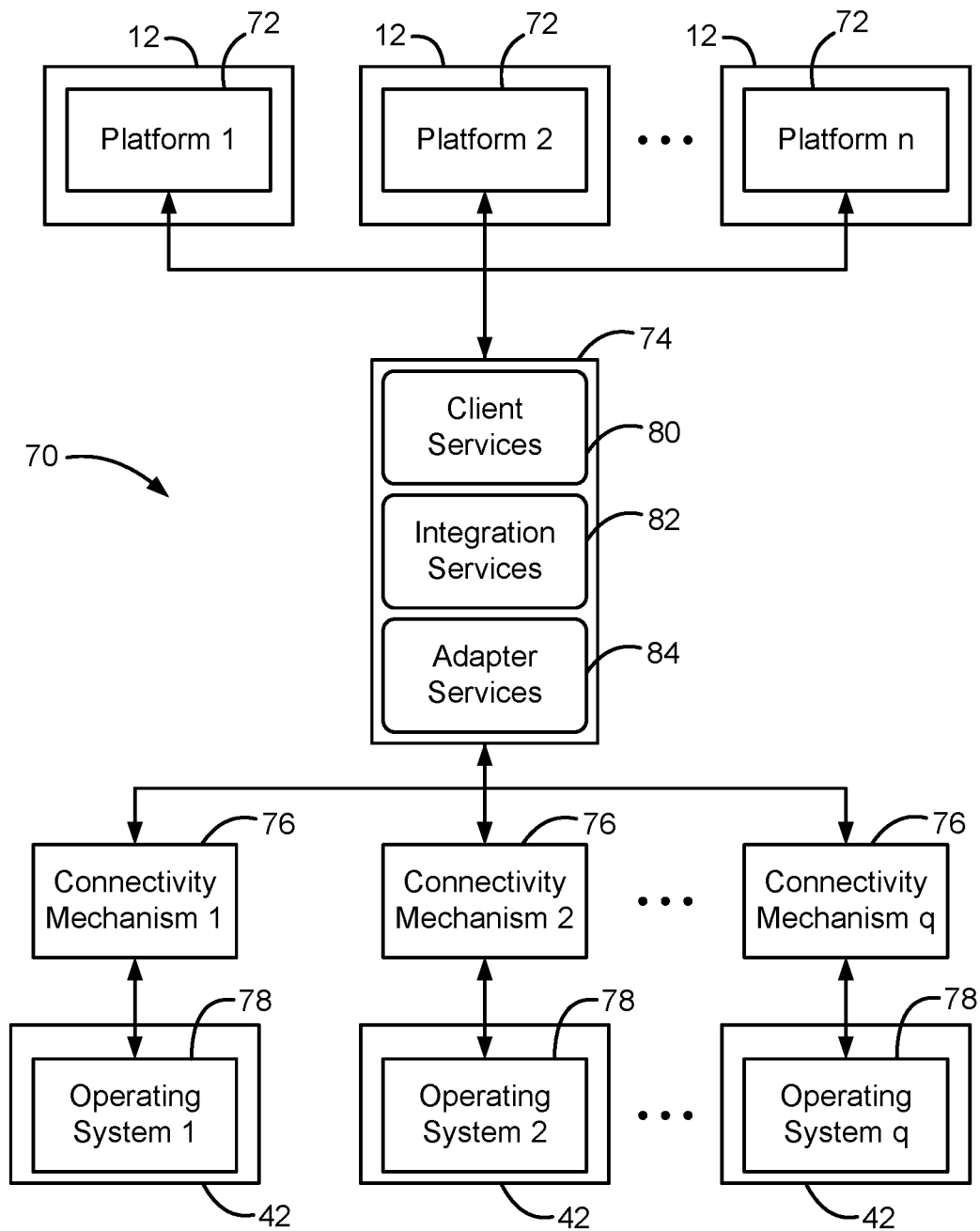
FIG. 3 is a functional block diagram of components that can be used to implement the present disclosure.
Figure 4:
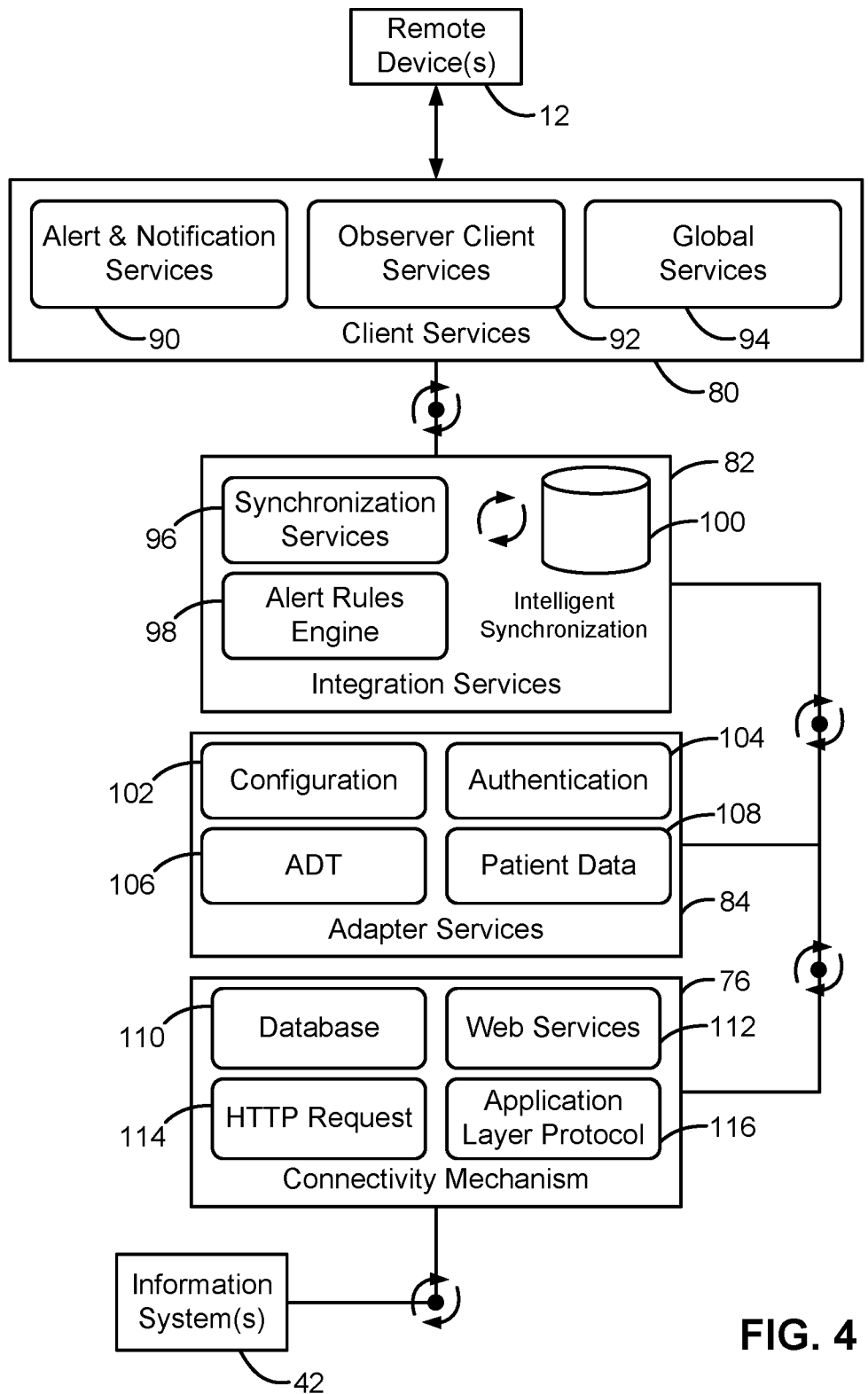
FIG. 4 is a more detailed view of the functional block diagram of FIG. 2.

Referring now to FIGS. 3 and 4, an exemplar software component, or module structure 70 to implement the features of the present disclosure will be described in detail. The exemplar structure enables patient data and patient information to be communicated to/from, and to be synchronized between the information system 42 and the mobile device 12, regardless of the operating system, or platform, operating on the mobile device 12. Exemplar platforms include, but are not limited to, RIM Blackberry, Apple iPhone, MS Pocket PC 2003, Win Mobile 5.x (Pocket PC, Smartphone), Win Mobile 6.x (standard, professional) and/or any platforms to be developed (e.g., Google Android, and Palm PRE).

FIG. 3 illustrates an overview of the exemplar module structure 70, which includes a platform 72, or operating system, of the mobile device 12, intermediary components 74, a connectivity mechanism 76, and an operating system 78 of the information system 42. In this arrangement, the mobile device 12 is a client that executes a client application thereon. The intermediary components 74 are resident on the DMS 60, 60', and include a client services module 80, an integration services module 82, and an adapter services module 84. The DMS 60, 60' functions as an intermediary between the platform 72 resident on the mobile device 12 and the operating system 78 of the information system 42. A plurality of platforms 72 is illustrated to exemplify the ability of the DMS 60, 60' to transfer data to and from any platform 72 operating on the mobile device 12. The connectivity mechanism 76 enables communication between the DMS 60, 60' and a particular information system 42. A plurality of connectivity mechanisms 76 and corresponding operating systems 78 is illustrated to exemplify the ability of the DMS 60, 60' to transfer data to and from any operating system 78 on the information system 42.

In the exemplar structure illustrated in FIG. 4, the client services module 80 includes an alert and notification services module 90, an observer client services module 92, and a global services module 94. The integration services module 82 includes a synchronization services module 96, and an alert engines rule 98. The synchronization services module 96 can communicate with a synchronization database 100 to provide so-called intelligent synchronization. The adapter services module 84 includes a configuration module 102, an authentication module 104, an admission, discharge and transfer (ADT) module 106, and a patient data module 108.

The alert and notification services module 90 sends alerts and/or notifications to the mobile device 12, as discussed in further detail below. The observer client services module 92 facilitates communication between client applications, running on the mobile device 12, and backend server components that provide access to application data. The observer client services module 92 transmits data through a formatted request, and receives data in a proprietary data format. An exemplar data format includes, but is not limited to, JavaScript Object Notation (JSON), which is a lightweight computer data interchange format that provides a text-based, human-readable format for representing simple data structures and associative arrays, called objects). The global services module 94 communicates with the client running on the mobile device 12 and performs registration and client application configuration settings. Client application settings can be customized by the user of the mobile device 12, and the facility 40 and/or facility systems 18, 20, for which the mobile device 12 is configured to receive data.

The integration services module 82 is responsible for routing requests that are received from the observer client services module 92 to retrieve and package requested data, and to send a corresponding response. More specifically, the integration services module 82 requests data from the adapter services module 84, or from the synchronization database 100 depending on how the particular DMS 60, 60' is configured. If the DMS 60, 60' is configured to use a vendor adapter, the request goes directly to the adapter services module 84 to retrieve the data. If the DMS 60, 60' is configured for synchronization, then the data is retrieved from the synchronization database 100. The synchronization services module 96 communicates with the adapter services module 84 to maintain the synchronization database 100 current using intelligent synchronization.

Intelligent synchronization is synchronization executed based on variable configuration parameters, which enable the possibility of only some of the patient data and/or patient information to be synchronized as opposed to all of the available data being continuously synchronized. By using custom business rule logic to intelligently determine which patient data and/or information should be synchronized, and which patient data and/or information should be synchronized, the DMS 60, 60' functions more efficiently and can service an increased number of clients and configurations. By way of non-limiting example, prior to a user logging on to the DMS 60, 60' via the mobile device 12, no specific patient data and/or information is synchronized. Instead, only a patient census list and specific data elements corresponding to particular patients 50 are synchronized between the DMS 60, 60' and the information system(s) 42. Once the user logs on, and selects a particular patient 50 to review, the synchronization services begin synching all of the available patient data and/or information for that particular patient 50. Consequently, subsequent reviews of the particular patient 50 are much faster, because the patient data and/or information has been synchronized.

The adapter services module 84 is the mechanism that retrieves data from the information system 42, through the connectivity mechanism module 76, and that structures the data for the DMS 60, 60'. The data is formatted and rules are applied for the specific DMS 60, 60', for which the adapter has been written, regardless of whether the data is directly requested for a client through the integration services module 82, or is retrieved through the synchronization services module 96. The configuration module 102 captures configuration settings used by the information system(s) 42. The configuration module 102 can use already existing configuration information so that it does not have to be replicated in the DMS 60, 60'. By way of non-limiting example, all of the patient beds of a particular facility 40, and to which unit(s) they belong are typically stored in the information system(s) 42. The configuration module 102 reduces, or obviates manual effort in entering the configuration information. The configuration module 102 can also prevent problems from occurring when a configuration change is made in the information system(s) 42, but a system administrator forgets to make the change in the DMS 60, 60'.

The authentication module 104 handles the authentication needs of the DMS 60, 60', which can include, but are not limited to active directory authentication, vendor authentication, device ID restrictions, device phone number restrictions, and any combination thereof. Each facility system 18, 20 and/or facility 40 is configured to authenticate using any combination of such authentication mechanisms. Device ID restriction is the ability for an authentication service to look at a pre-configured list of device ID's, associated with respective mobile devices 12, that are authorized to connect to the facility system 18, 20 and/or facility 40, and only authorizes call from software client that originate with that device ID (i.e., from the particular mobile device 12). The device phone number restriction restricts access to mobile devices 12 that have a phone number that has been pre-configured in the authentication system.

The ADT module 106 enables the use of existing ADT interfaces within the facility system 18, 20 and/or facility 40 to obtain patient admission, discharge and transfer information in order to always know which patient is associated to which bed and/or unit. The patient data module 108 provides all waveform and non-waveform patient data and/or information from the information system(s) 42 to the DMS 60, 60'. The patient data module 108 can also provide all waveform and non-waveform acquired from a data acquisition system such as the AirStrip data collector or an independent data collecting system including but not limited to Capsule Technologies' Data Captor system. This includes, but is not limited to, all nursing charting information as well as any automated means of data collection used by the information system(s) 42.

In the exemplar structure illustrated in FIG. 4, each connectivity mechanism module 76 includes a database module 110, a web services module 112, a request module 114, and an application layer protocol module 116. By way of non-limiting example, the request module 114 can manage HTTP requests, and/or the application layer protocol can include the health level seven (HL7) application layer protocol. The connectivity mechanism module 76 enables the DMS 60, 60' to connect to and communicate with the particular information system 42. In some implementations, the connectivity mechanism module 76 can include application protocol interfaces (APIs), through which it communicates with the information system 42. In other implementations, the connectivity mechanism module 76 can directly access the information system 42.

As discussed at the outset, the present disclosure provides a healthcare provider, or user of the mobile device 12, with secure, remote access to patient data and/or patient information. As used herein, the term patient data refers to physiological data that can be obtained from the patient monitoring device(s), and/or physiological patient data that is input into the information system 42 by a local healthcare provider (e.g., a nurse, or physician). The term patient information refers to information corresponding to a particular patient that is input into the information system 42 by the local healthcare provider. Exemplar patient information can include, but is not limited to, the patient's name, the name of the doctor(s) assigned to the patient, the nurse(s) assigned to the patient, a facility identification, a patient bed identification, a summary of key patient data, and/or chart annotations. In the exemplar case of a maternity patient, the key patient data can include, but is not limited to, delivery progress information such as cervical exam status, membrane status, gravida, para, epidural status, and/or whether the patient is attempting a vaginal birth after cesarean (VBAC).

The patient data and/or patient information provided to the remotely located user can be provided in real-time data, and/or as historical data and information. The patient data and/or patient information is communicated between the mobile device 12 and the DMS 60, 60' using a secure connection that is established over the network 16. A secure log-in, or sign-on process is provided, which is preferably compliant with the provisions of the Health Insurance Portability and Accountability Act (HIPAA). The secure sign-on authenticates the identity of the user of the mobile device 12 based on a unique user ID and password combination. Both the user ID and the password must be correct in order to establish the secure communication between the mobile device 12 and the DMS 60, 60'. Implementations of sign-on and authentication processes are described in further detail below.

A census, or patient list is provided to the mobile device 12, which captures a variety of the information and/or data described herein that is associated with each of one or more monitored patients 50. Strip charting is also provided, in which patient data and/or information can be presented to the user in graphical form. In the exemplar case of a maternity patient, a fetal strip and maternal contraction information can be provided for a particular patient 50. More specifically, the particular patient 50 is selected from the patient list, and the patient information and/or data is subsequently presented. The presented information and/or data can include a fetal strip and maternal contraction waveform, the patient name, the hospital name, the patient room and/or bed number, and the date and time. The strip charting can provide a real-time view of the patient data, as well as a historical view of the patient data. More specifically, the waveform display can be updated in real-time, such that the user of the mobile device 12 observes the patient data as it occurs and/or is recorded. The user can scroll through the waveform display, to view historical patient data, as described in further detail below.

Several navigation features can be provided that enable the user to manipulate a view of the waveform display. In some implementations, the user can zoom in/out of the displayed image. In this manner, the user can view very specific waveform information, and/or other waveform micro-characteristics by zooming in, for example, and/or can view patterns or other waveform macro-characteristics by zooming out, for example. In some implementations, the user can scroll forward or backward through the waveform display. In this manner, the user can view historical patient data.

A patient data display can also be provided. In some implementations, the patient data display can overlay the strip charting described herein. In other implementation, the patient data display can be provided as an overlay, and/or as a separate display. The patient data display can include, but is not limited to, the patient's name, age, fetal gestation, gravida, parity, cervical exam information, and physician name.

Figure 5:
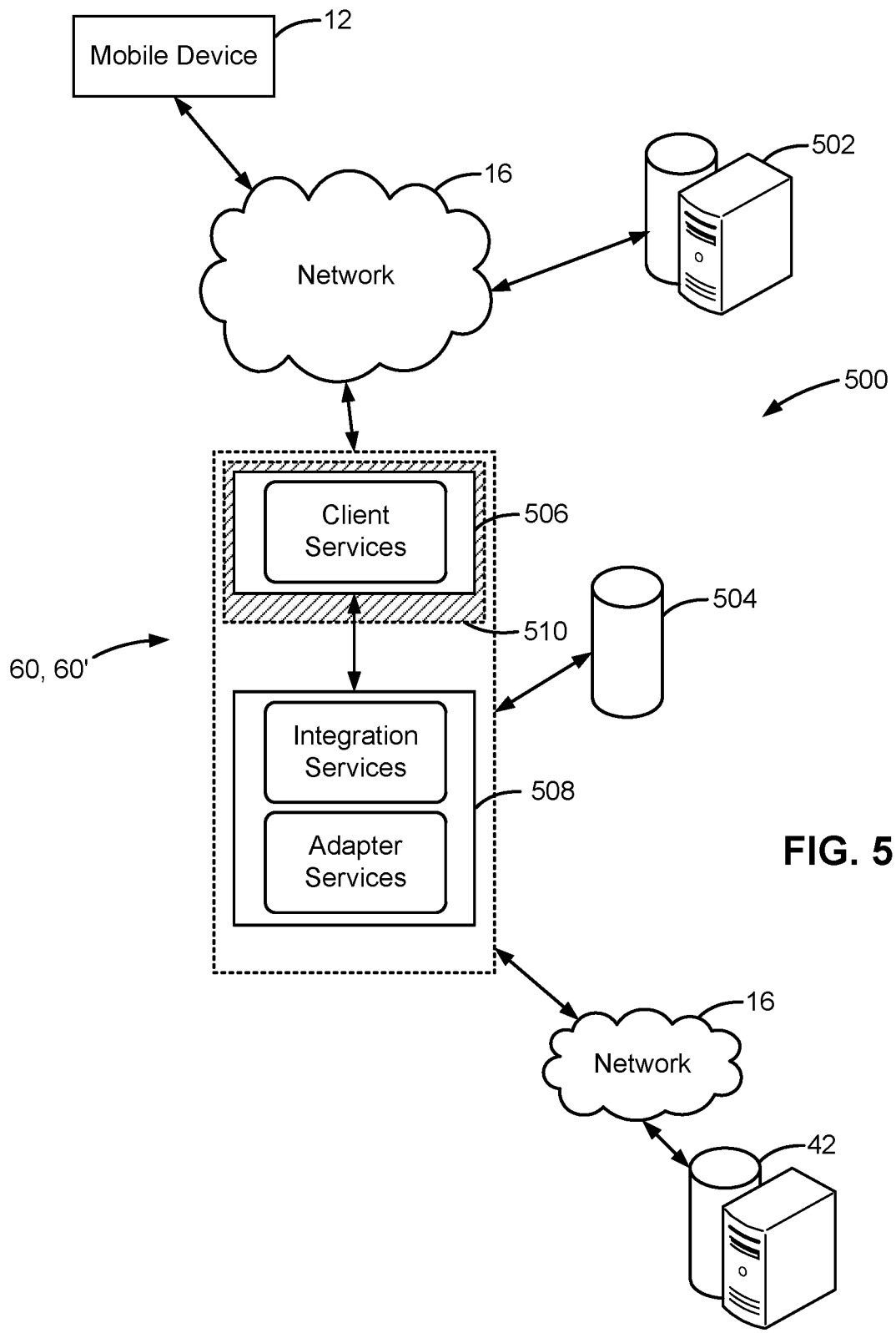
FIG. 5 is a schematic illustration of an authentication system.

Implementations of the present disclosure can be realized on any one of a number of operating systems, or platforms 72 associated with the particular mobile device 12. As discussed above with reference to FIGS. 3 and 4, exemplar platforms include, but are not limited to, RIM Blackberry, Apple iPhone, MS Pocket PC 2003, Win Mobile 5.x (Pocket PC, Smartphone), Win Mobile 6.x (standard, professional) and/or any platforms to be developed (e.g., Google Android, and Palm PRE). Referring now to FIG. 5 exemplar implementations of the present disclosure will be described with reference to screen-shots of an exemplar mobile device 12. The mobile device 12 of the instant example includes a mobile device, such as a cellular telephone, or smartphone, that includes an exemplar platform (e.g., Apple iPhone). It is appreciated, however, that implementations of the present disclosure can be executed on any type of mobile device 12, and/or using any type of platform 72 that is supported by the mobile device 12. It is appreciated that the screen-shots illustrated and described herein are merely exemplar in nature, and are not exhaustive of the functionality and features provided in implementations of the present disclosure.

Implementations of the present disclosure provide an authentication process for authenticating, or validating, the user of a mobile device and the mobile device itself. Specifically, the authentication process authenticates the user and the mobile device before establishing a session between the mobile device and a CIS and enabling user access to information and data provided. Prior to accessing the CIS, the user of the mobile device registers the mobile device with a device registration system, discussed in further detail below. As a result of the registration, the user is registered and one or more technical factors associated with the mobile device are stored to a validation database. The one or more technical factors include a unique device identification (ID) associated with a particular device, and a telephone number registered to the user and the mobile device, in the case where the mobile device includes a mobile telephone and/or smartphone.

When the user seeks access to patient information and data using the mobile device, the user initiates execution of a client application on the mobile device. The client application prompts the user for credentials. The credentials include a username and password. These credentials correspond to credentials that the user has already established with the facility for allowing the user access to the information system. The client application generates a logon request that is transmitted to the DMS, as discussed in further detail below. The logon request includes the credentials and at least one technical factor (i.e., the device ID and/or telephone number).

Referring now to FIG. 5, an authentication system 500 in accordance with implementations of the present disclosure will be described. The authentication system 500 includes a mobile device 12, a network 16, a DMS 60, 60', an information system 42, an authentication server system 502, and a validation database 504. The DMS 60, 60' includes a server 506 and an application server 508. The server 506 operates in a perimeter network, or demilitarized zone (DMZ) 510 to inhibit unauthorized access to other servers and server systems through the server 506. In some implementations, the server 506 and the application server 508 can be executed on the same physical device, and be logically separated from one another. In some implementations, the server 506 and the application server 508 can be executed on different devices, such that they are both logically and physically separate from one another.

The server 506 handles communication between external networks and the DMS 60, 60'. For example, the server 506 can execute the client services 80 discussed above with reference to FIGS. 3 and 4. The server 508 handles communication between the DMS 60, 60' and one or more information systems 42 associated with one or more facilities 40. For example, the application server 508 can execute the integration services 82, the adapter services 84, and/or the connectivity mechanism 76 discussed above with respect to FIGS. 3 and 4.

The logon request is transmitted to the DMS 60, 60' from the mobile device 12 over the network 16. For example, the logon request can be transmitted using hypertext transfer protocol secure (HTTPS), which includes the hypertext transfer protocol (HTTP) with the secure sockets layer (SSL) or the transport layer security (TLS) protocol to provide encryption and secure identification of the server 506. The server 506 checks the technical factor of the device against data provided in the validation server 504. Specifically, the validation database 504 stores technical factor information corresponding to mobile devices that have been registered using the registration server 504. For example, the device ID and/or telephone number are checked against device IDs and telephone numbers of registered mobile devices stored in the validation database 504. If the technical factor does not correspond to a mobile device that has been registered as a valid mobile device, the logon request is denied. If the logon request is denied, a corresponding message can be transmitted to the mobile device 12 for display to the user. If the technical factor corresponds to a mobile device that has been registered as a valid mobile device, the logon request is transmitted from the server 506 to the application server 508.

In some implementations, the application server 508 authenticates the credentials based on data retrieved from the information system 42. Specifically, the application server 508 can retrieve authentication information from the information system 42, based on information provided in the logon request. The authentication server 508 compares the credentials provided in the logon request to the authentication information to determine whether the credentials are valid. In some implementations, the application server 508 forwards the logon request, or at least the credentials provided in the logon request, to the information system 42. The information system 42 compares the credentials provided in the logon request to the authentication information stored at the information system 42 to determine whether the credentials are valid.

If the credentials are not valid, the logon request is denied and a corresponding message is displayed to the user at the mobile device 12. If the credentials are valid, the logon request is accepted, and a session is established between the mobile device and the DMS 60, 60'. Specifically, during the session, the mobile device 12 can retrieve patient information and data from the DMS 60, 60', the patient information and data being provided to the DMS 60, 60' by the information system 42. The mobile device 12 can provide information and data to the DMS 60, 60', which information can be forwarded to and stored on the information system 42.

Figure 6:
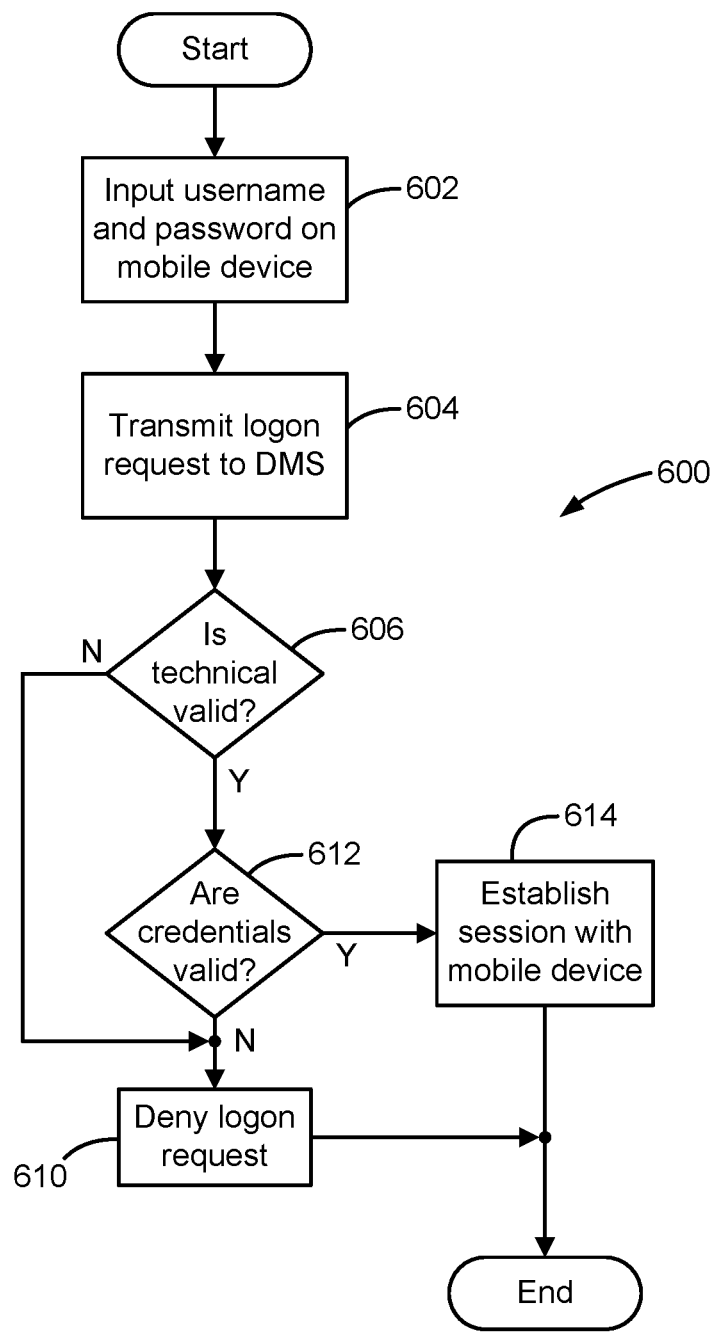
FIG. 6 is a flowchart illustrating exemplar steps in accordance with implementations of the present disclosure.

Referring now to FIG. 6, exemplar steps 600 that can be executed to authenticate a user of a mobile device and the mobile device will be described. In step 602, a username and password are input to a mobile device. For example, the username and password can be input by a user in response to a logon prompt issued by an application executed on the mobile device. In step 604, a logon request is transmitted from the mobile device to a DMS. For example, one or more processors of the mobile device can generate a logon request based on the input. In some implementations, the logon request can include the username, the password and one or more technical factors (e.g., device ID, telephone number).

In step 606, it is determined whether the one or more technical factors of the logon request are valid technical factors. For example, the DMS can access a validation database using information provided in the logon request as an index to the database. In some implementations, the DMS can use the username as an index to retrieve a device ID and/or telephone number from the database. If the device ID and/or telephone number from the database corresponds to the device ID and/or telephone number provided in the logon request, the technical factors are deemed valid. In some implementations, the DMS can use the one or more technical factors as an index, or indices to retrieve a username from the database. If the username from the database corresponds to the username provided in the logon request, the technical factors are deemed valid.

If the technical factor(s) is valid, the steps continue in step 612. If the technical factor(s) is not valid, the logon request is denied in step 610, and the steps end. For example, the DMS can generate an access denied message and transmit the message to the mobile device for display to the user.

In step 612, it is determined whether the credentials are valid. The credentials include the username and password provided in the logon request. In some implementations, the DMS (e.g., the application server of the DMS) can retrieve authentication information from the information system, and can determine whether the credentials are valid. In some implementations, the DMS can provide the logon request, or at least the credentials provided in the logon request, to the information system, the information system determining whether the credentials are valid. For example, the information system can access a credentials database using the username as an index to retrieve a corresponding password. If the username does not correspond to a username stored in the database, the credentials are not deemed valid. If the username corresponds to a username stored on the database, a password associated with the stored username is retrieved. If the password from the database corresponds to the password of the credentials, the credentials are deemed valid. If the password from the database does not correspond to the password of the credentials, the credentials are deemed invalid. If the credentials are not valid, the logon request is denied in step 610, and the steps end. If the credentials are deemed valid, a session is established to provide patient information and data from the information system to the mobile device in step 614, and the steps end.

The present disclosure can be implemented in digital electronic circuitry, or in computer hardware, firmware, software, or in combinations thereof. The invention can be implemented as a computer program product, i.e., a computer program tangibly embodied in an information carrier, e.g., in a machine-readable storage device, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Such a computer program can include modules and/or code segments for executing one or more of the features, aspects and/or implementations provided herein.

Method steps of the present disclosure can be performed by one or more programmable processors executing a computer program product to perform functions of the present disclosure by operating on input data and generating output. By way of one non-limiting example, a computer program product can include modules and/or code segments corresponding to each of the method steps, aspects and/or features provided herein. Method steps can also be performed by, and apparatus of the present disclosure can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks such as internal hard disks and removable disks; magneto-optical disks; and CD-ROM and DVD-ROM disks. The processor and the memory can be supplemented by, or incorporated in special purpose logic circuitry.

The present disclosure can be implemented in a system including, but not limited to the exemplar systems described herein, which include a back-end component, e.g., as a data server, or that includes a middleware component, e.g., an application server, or that includes a front-end component, e.g., a client device, such as the mobile device 12, having a graphical user interface or a Web browser through which a user can interact with an implementation of the invention, or any combination of such back-end, middleware, or front-end components. The components of the system can be interconnected by any form or medium of digital data communication, e.g., a communication network.

A number of embodiments have been described. Nevertheless, it will be understood that various modifications may be made without departing from the spirit and scope of the disclosure. For example, steps of the invention can be performed in a different order and still achieve desirable results. Accordingly, other embodiments are within the scope of the following claims.

What is claimed is:

1. A server for managing transmission of patient data, the server comprising:
    a web server provided inside of a demilitarized zone (DMZ) to inhibit unauthorized access to other servers through the web server, the web server comprising:
        a client services module configured to receive a logon request, the logon request comprising credentials associated with a user and at least one technical factor associated with a mobile device, wherein the credentials comprise a username and a password, and
        a database synchronization component coupled to the client services module and configured to access a validation database based on one of the at least one technical factor and the credentials,
        the web server being configured to:
            check the at least one technical factor based on information provided by the validation database, and
            in response to determining that the at least one technical factor corresponds to a device that has been registered as a valid mobile device, forward the logon request; and
    an application server provided outside of the DMZ, the application server comprising:
        an adapter services module coupled to the database synchronization component and configured to:
            receive the logon request from the web server,
            retrieve, from a clinical information system of a medical facility, authentication information corresponding to the user by using the username as an index to retrieve a corresponding stored password,
            compare the credentials to the authentication information corresponding to the user to generate a comparison result,
            determine that the user is authorized to access the patient data based on the comparison result; and
        an integration services module coupled to the adapter services module and configured to perform operations in response to authenticating the mobile device and authenticating the user, the operations comprising:
            establishing a session to communicate the patient data between the clinical information system and the mobile device,
            retrieving the patient data from the clinical information system,
            processing the patient data based on one or more configuration settings used by the clinical information system to generate processed patient data, and
            transmitting the processed patient data to the mobile device for display using a connectivity mechanism matching an operating system of the mobile device, the connectivity mechanism being of a plurality of connectivity mechanisms, each connectivity mechanism of the plurality of connectivity mechanisms being specific to a respective operating system.

2. The server of claim 1, wherein the server is remotely located from the medical facility.

3. The server of claim 1, wherein the web server operates in a perimeter network and provides services to the application server and an external network, the perimeter network limiting access from the external network to the application server.

4. The server of claim 1, wherein the web server and the application server are provided on a common physical device and are logically separated from one another.

5. The server of claim 1, wherein the web server and the application server are provided on respective physical devices to be physically separate from one another.

6. The server of claim 1, wherein the mobile device comprises a mobile phone, and the at least one technical factor further comprises a telephone number associated with the mobile device.

7. The server of claim 1, wherein the at least one technical factor comprises a device identification associated with the mobile device.

8. The server of claim 1, the adapter services module is further configured to transmit the credentials to the clinical information system in response to determining that the mobile device is authorized to access the patient data.

9. The server of claim 1, wherein the patient data comprises real-time updated data generated by a patient monitoring device that is in communication with the clinical information system.

10. The server of claim 1, wherein the adapter services module comprises a configuration module, an authentication module, an admission module, a discharge module, a transfer module, and a patient data module.

11. An authentication server system for managing access to patient data, the authentication server system comprising:
    a web server provided inside of a demilitarized zone (DMZ) to inhibit unauthorized access to other servers through the web server, the web server comprising first physical hardware and being configured to:
        receive a logon request comprising credentials associated with a user and at least one technical factor associated with a mobile device, wherein the credentials comprise a username and a password,
        access a validation database to retrieve validation information,
        check the at least one technical factor based on the validation information provided by the validation database, and
        in response to determining that the at least one technical factor corresponds to a device that has been registered as a valid mobile device, forward the logon request; and an application server provided outside of the DMZ, the application server comprising second physical hardware and being configured to:
receive the logon request from the web server,
retrieve, from a clinical information system of a medical facility, authentication information corresponding to the user by using the username as an index to retrieve a corresponding stored password,
compare the credentials to the authentication information corresponding to the user to generate a comparison result,
determine that the user is authorized to access the patient data based on the comparison result, and
establishing a session to communicate the patient data between the clinical information system and the mobile device.

12. The authentication server system of claim 11, wherein the authentication server system server is remotely located from the medical facility.

13. The authentication server system of claim 11, wherein the web server operates in a perimeter network and provides services to the application server and an external network, the perimeter network limiting access from the external network to the application server.

14. The authentication server system of claim 11, wherein the web server and the application server are provided on a common physical device and are logically separated from one another.

15. The authentication server system of claim 11, wherein the web server and the application server are provided on respective physical devices to be physically separate from one another.

16. The authentication server system of claim 11, wherein the mobile device comprises a mobile phone, and the at least one technical factor further comprises a telephone number associated with the mobile device.

17. The authentication server system of claim 11, wherein the at least one technical factor comprises a device identification associated with the mobile device.

18. The authentication server system of claim 11, wherein the patient data comprises real-time updated data generated by a patient monitoring device that is in communication with the clinical information system.

* * * * *